United States Patent [19]

Mukaiyama et al.

[11] 4,206,310
[45] Jun. 3, 1980

[54] PROCESS FOR THE PREPARATION OF ESTERS

[75] Inventors: Teruaki Mukaiyama; Masahiro Usui, both of Tokyo; Kazuhiko Saigo, Chiba; Eiichiro Shimada, Narashino, all of Japan

[73] Assignee: Sumitomo Chemical Company, Limited, Osaka, Japan

[21] Appl. No.: 940,757

[22] Filed: Sep. 8, 1978

Related U.S. Application Data

[63] Continuation of Ser. No. 724,846, Sep. 20, 1976, abandoned.

[30] Foreign Application Priority Data

Sep. 27, 1975 [JP] Japan .................. 50-117038

[51] Int. Cl.$^2$ ............................................. C07C 67/08
[52] U.S. Cl. ...................................... 560/105; 560/98; 560/103; 560/106; 560/204; 560/254; 560/265
[58] Field of Search ............... 560/254, 106, 103, 105, 560/98, 204, 265

[56] References Cited

FOREIGN PATENT DOCUMENTS 1958954  3/1971  Fed. Rep. of Germany .......... 560/103

OTHER PUBLICATIONS

Mukaiyama et al., as cited in Chem. Abstracts, 84, 73839z (1976).
Mukaiyama et al., Chemistry Letters, 1975, pp. 1045–1048 (1975) (Oct.).

Primary Examiner—Jane S. Myers
Attorney, Agent, or Firm—Stevens, Davis, Miller & Mosher

[57] ABSTRACT

An improved process for producing an ester from a carboxylic acid and an alcohol which comprises reacting said carboxylic acid with said alcohol by the use of a 1-substituted-2-halopyridinium salt or a 1-substituted-2-haloquinolinium salt as a condensing agent in the presence of a hydrogen halide captor. According to this process, various esters, even if they have some steric hindrances, may be obtained in good yields.

1 Claim, No Drawings

PROCESS FOR THE PREPARATION OF ESTERS

This is a continuation of application Ser. No. 724,846 filed Sept. 20, 1976 now abandoned.

The present invention relates to an improved process for producing carboxylic esters. More particularly, this invention pertains to a process for producing carboxylic esters by esterification of a carboxylic acid and an alcohol using as a condensing agent a 1-substituted-2-halopyridinium salt or 1-substituted-2-haloquionolinium salt in the presence of a hydrogen halide captor.

So far, it has been well known that esterification is one of the most important and basic synthetic methods for the production of esters and that in carrying out esterification some arrangements such as distillation of the ester or water as formed, the use of an excess amount of either an alcohol or an acid or removal of water with a dehydrating agent are needed to obtain the objective ester in high yields. However, these methods are not always satisfactory in view of the equipments or reaction conditions involved therein.

As the result of an intensive study, it has been found that by the use of a 1-substituted-2-halopyridinium salt or 1-substituted-2-haloquionolinium salt as a condensing agent in the presence of a hydrogen halide captor esterification of a carboxylic acid and an alcohol can be carried out under mild reaction conditions and in very high yields. According to the esterification of this invention carboxylic esters may be obtained in high yields from equimolar amounts of an alcohol and an acid. Furthermore, this esterification can be applied to such alcohols and acids that were difficult to esterify due to steric hindrance by the conventional procedures and even if this esterification is applied to such acids or alcohols, relatively high yields of esters may be obtained.

The 1-substituted-2-halopyridinium salts used in this invention may be represented by the formula:

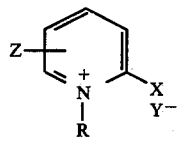

wherein R is $C_1$–$C_6$ alkyl, allyl, $C_3$–$C_6$ cycloalkyl($C_1$–$C_2$)alkyl, 2-oxo-($C_1$–$C_6$)alkyl, aryl-($C_1$–$C_6$)alkyl or aryl-substituted 2-oxo-($C_1$–$C_6$)alkyl; X is halogen; $Y^-$ is halide ion, methylsulfate ion, p-toluenesulfonate ion, perchlorate ion or tetrafluoroborate ion; and Z is $C_1$–$C_6$ alkyl, nitro, halogen or $C_1$–$C_6$ alkoxy.

The 1-substituted-2-haloquinolinium salts may be represented by the formula:

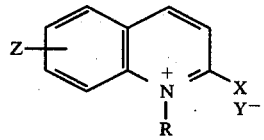

wherein R, X, $Y^-$ and Z are as defined above.

In the significances as described above, "aryl-substituted 2-oxo-($C_1$–$C_6$)alkyl" and "aryl-($C_1$–$C_6$)alkyl" may preferably include phenyl-substituted-2-oxo-($C_1$–$C_6$)alkyl and phenyl-($C_1$–$C_6$)alkyl.

Among the 1-substituted-2-halopyridinium salts and the 1-substituted-2-haloquionolinium salts, the followings are particularly preferred: 2-Chloro-1-methylpyridinium iodide, 2-iodo-1-methylpyridinium methyl sulfate, 2-chloro-1-ethylpyridinium bromide, 1-benzyl2-chloropyridinium bromide, 2-chloro-1-phenacyl-pyridinium chloride, 2-fluoro-1-methylpyridinium p-toluenesulfonate, 2-bromo-1-methylpyridinium perchlorate, 1-ethyl-2-iodoquionolinium iodide, 2-chloro-1-ethyl-4-methoxypyridinium tetrafluororborate and 2,6-dichloro-1-ethylpyridinium tetrafluoroborate.

The hydrogen halide captors used in this invention may be a tertiary amino of the formula:

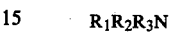

$R_1R_2R_3N$ wherein $R_1$, $R_2$ and $R_3$ each are $C_1$–$C_{15}$ alkyl, allyl or $C_3$–$C_6$ cycloalkyl-($C_1$–$C_2$)alkyl; or betaines which mean in this specification compounds having an anion and a cation in their molecule.

The typical examples of said tertiary amines are triethylamine, tri-n-butylamine, N,N-dimethylbutylamine, N,N-dimethylcyclohexylamine, lutidine, collidine, N-methylpyrrolidine, N-methylmorpholine, 1,5-diazabicyclo[4,3,0]nonene-5, 1,4-diazabicyclo[2,2,2]octane and 1,5-diazabicyclo[5,4,0]undecene-5.

Preferred examples of the betaines are 3,4-dihydro-2H-pyrido[1,2-a]pyrimidin-2-one, triethylammonium acetate, 1-oxonianaphthalene-7-carboxylate, and (1-methyl-4-pyridinio)acetate.

In carrying out the esterification of this invention, the amount of the 1-substituted-2-halopyridinium salt or 1-substituted-2-haloquinolinium salt used is not particularly limited, but good results may be obtained when they are used in an amount of one to five times as much as the carboxylic acid by mole. The mixing molar ratio of the hydrogen halide captor to the 1-substituted-2-halopyridinium salt or 1-substituted-2-haloquinolinium salt is not particularly limited, but the preferred ratio is 2:1.

The esterification of this invention may preferably be carried out in the presence of an anhydrous organic solvent preferred examples of which are ethyl ether, toluene, tetrahydrofuran, benzene, xylene, acetonitrile, 1,2-dimethoxyethane, methylene dichloride, chloroform or carbon tetrachloride. The reaction of this invention may be carried out at a temperature of 0° C. to the boiling point of the solvent used but the latter is preferable.

The carboxylic acids and the alcohls used in the present invention are not particularly limited.

The carboxylic acids may be mono-, di- or poly-carboxylic acids, oxocarboxylic acids or aminocarboxylic acids and the alcohols may be mono-, di- or poly-alcohols, oxoalcohols or aminoalcohols.

The following examples are given to illustrate the invention more presicely but they should not be construed to limit the scope of the invention.

EXAMPLE 1

To a suspended $CH_2Cl_2$ (2 ml) solution of 2-bromo-1-methylpyridinium iodide (720 mg, 2.4 mmol) was added a mixture of benzyl alcohol (216 mg, 2.0 mmol), phenylacetic acid (272 mg, 2.0 mmol) and tri-n-butylamine (888 mg, 4.8 mmol) in $CH_2Cl_2$ (2 ml), and the resulting mixture was refluxed for 3 hours. After evaporation of the solvent, the residue was separated by silica gel column chromatography, and benzyl phenylacetate was isolated in 97% yield.

EXAMPLE 2

To a CH$_2$Cl$_2$ (2ml) solution of 2-chloro-1-ethyl-4-methoxypryridinium tetrafluoroborate (296 mg, 1.2 mmol) was added a mixture of benzyl alcohol (108 mg, 1.0 mmol), phenylacetic acid (136 mg, 1.0 mmol) and triethylamine (243 mg, 2.4 mmol) in CH$_2$Cl$_2$ (2 ml), and the resulting mixture was refluxed for 3 hours. After evaporation of the solvent, the residue was separated by silica gel column chromatography, and benzyl phenylacetate was isolated in 95% yield.

EXAMPLE 3

To a suspended ethyl ether (2 ml) solution of 2-chloro-1-methylpyridinium iodide (306 mg, 1.2 mmol) was added a mixture of benzyl alcohol (108 mg, 1.0 mmol), phenylacetic acid (136 mg, 1.0 mmol) and tri-n-butylamine (444 mg, 2.4 mmol) in ethyl ether (2 ml), and the resulting mixture was refluxed for 3 hours. After evaporation of the solvent, the residue was separated by silica gel column chromatography, and benzyl phenylacetate was isolated in 97% yield.

EXAMPLE 4

To a suspended CH$_2$Cl$_2$ (2 ml) solution of 2-chloro-1-methylpyridinium iodide (306 mg, 1.2 mmol) was added a mixture of benzyl alcohol (108 mg, 1.0 mmol), phenylacetic acid (136 mg, 1.0 mmol) and 2,6-lutidine (257 mg, 2.4 mmol) in CH$_2$Cl$_2$ (2 ml), and the resulting mixture was refluxed for 3 hours. After evaporation of the solvent, the residue was separated by silica gel column chromatography, and benzyl phenylacetate was isolated in 98% yield.

EXAMPLE 5

To a suspended toluene (2 ml) solution of 2-bromo-1-methylpyridinium iodide (720 mg, 2.4 mmol) was added a mixture of tert-butyl alcohol (148 mg, 2.0 mmol), phenylacetic acid (272 mg, 2.0 mmol) and tri-n-butylamine (888 mg, 4.8 mmol) in toluene (2 ml), and the resulting mixture was refluxed for 3 hours. After evaporation of the solvent, the residue was separated by silica gel column chromatography, and tert-butyl phenylacetate was isolated in 82% yield.

EXAMPLE 6

To a CH$_2$Cl$_2$ (2 ml) solution of 2,6-dichloro-1-ethylpyridinium tetrafluoroborate (630 mg, 2.4 mmol) was added a mixture of ethyl alcohol (92 mg, 2.0 mmol), phenylacetic acid (272 mg, 2.0 mmol) and tri-n-butylamine (888 mg, 4.8 mmol) in CH$_2$Cl$_2$ (2 ml), and the resulting mixture was refluxed for 3 hours. After evaporation of the solvent, the residue was separated by silica gel column chromatography, and ethyl phenylacetate was isolated in 90% yield.

EXAMPLE 7

To a suspended CH$_2$Cl$_2$ (2 ml) solution of 2-bromo-1-methylpyridinium (720 mg, 2.4 mmol) was added a mixture of cinnamyl alcohol (268 mg, 2.0 mmol), acetic acid (120 mg, 2.0 mmol) and tri-n-butylamine (888 mg, 4.8 mmol) in CH$_2$Cl$_2$ (2 ml), and the resulting mixture was refluxed for 3 hours. After evaporation of the solvent, the residue was separated by silica gel column chromatography, and cinnamyl acetate was isolated in 82% yield.

EXAMPLE 8

To a CH$_2$Cl$_2$ (2 ml) solution of 2-chloro-1-methylpyridinium p-toluenesulfonate (720 mg, 2.4 mmol) was added a mixture of benzyl alcohol (216 mg, 2.0 mmol), benzoic acid (244 mg, 2.0 mmol) and tri-n-butylamine (888 mg, 4.8 mmol) in CH$_2$Cl$_2$, and the resulting mixture was refluxed for 3 hours. After evaporation of the solvent, the residue was separated by silica gel column chromatography, and benzyl benzoate was isolated in 83% yield.

EXAMPLE 9

To a suspended toluene (2 ml) solution of 2-chloro-1-methylpyridinium iodide (306 mg, 1.2 mmol) was added a mixture of benzyl alcohol (108 mg, 1.0 mmol), pivalic acid (102 mg, 1.0 mmol) and tri-n-butylamine (444 mg, 2.4 mmol) in toluene (2 ml), and the resulting mixture was refluxed for 3 hours. After evaporation of the solvent, the residue was separated by silica gel column chromatography, and benzyl pivalate was isolated in 62% yield.

EXAMPLE 10

To a suspended CH$_2$Cl$_2$ (2 ml) solution of 1-ethyl-2-iodoquinolinium iodide (493 mg, 1.2 mmol) was added a mixture of benzyl alcohol (108 mg, 1.0 mmol), phenylacetic acid (136 mg, 1.0 mmol) and tri-n-butylamine (444 mg, 2.4 mmol) in CH$_2$Cl$_2$ (2 ml), and the resulting mixture was refluxed for 3 hours. After evaporation of the solvent, the residue was separated by silica gel column chromatography, and benzyl phenylacetate was isolated in 95% yield.

What is claimed is:

1. A process for producing an ester by esterification of a carboxylic acid and an alcohol in equimolar amounts which comprises carrying out the esterification by the use of at least one mole per mole of the carboxylic acid of 1-substituted-2-halopyridinium salt of the formula,

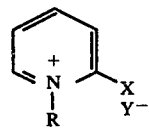

wherein R is C$_1$–C$_6$ alkyl, allyl, C$_3$–C$_6$ cycloalkyl-(C$_1$–C$_2$) -alkyl, 2-oxo-(C$_3$–C$_6$)alkyl, phenyl-(C$_1$–C$_6$)alkyl or phenyl-substituted 2-oxo-(C$_2$–C$_6$)alkyl, X is halogen, and Y$^-$ is halide ion, methyl-sulfate ion, p-toluenesulfonate ion, perchlorate ion or tetrafluoroborate ion, or 1-substituted-2-haloquinolinium salt of the formula,

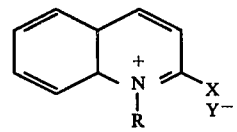

wherein R, X and Y$^-$ are as defined above, as a condensing agent, in the presence of at least 2 equimolar amounts per mole of the 1-substituted-2-halopyridinium salt or the 1-substituted-2-haloquinolinium salt of a tertiary amine of the formula, $R_1R_2R_3N$ wherein $R_1$, $R_2$ and $R_3$ each are $C_1$–$C_{15}$ alkyl, allyl or $C_3$–$C_6$ cycloalkyl, or an amine selected from the group consisting of lutidine, N-methylmorpholine, 1,5-diazabicyclo[4,3,0]nonene-5, 1,4-diazabicyclo[2,2,2]-octane and 1,5-diazabicyclo[5,4,0]undecene-5 in anhydrous organic solvent at a temperature of 0° C. to the boiling point of the solvent used.

* * * * *